United States Patent [19]

Kubicek et al.

[11] Patent Number: 5,536,692
[45] Date of Patent: Jul. 16, 1996

[54] ISOMERIZATION CATALYST AND USE THEREOF IN ISOMERIZATION OF SATURATED HYDROCARBONS

[75] Inventors: Donald H. Kubicek; An-hsiang Wu, both of Bartlesville, Okla.

[73] Assignee: Phillips Petroleum Company, Bartlesville, Okla.

[21] Appl. No.: 348,694

[22] Filed: Dec. 2, 1994

[51] Int. Cl.⁶ .................................................. B01J 27/13
[52] U.S. Cl. ................................. 502/230; 502/229
[58] Field of Search ............................... 502/107, 227, 502/229, 230

[56] References Cited

U.S. PATENT DOCUMENTS

| | | | |
|---|---|---|---|
| 2,900,425 | 8/1959 | Bloch et al. | 260/666 |
| 3,231,517 | 1/1966 | Bloch et al. | 252/442 |
| 3,755,140 | 8/1973 | Pollizer | 208/62 |
| 3,787,313 | 1/1974 | Pollitzer | 208/60 |
| 3,963,643 | 6/1976 | Germanas et al. | 252/442 |
| 4,149,993 | 4/1979 | Rao et al. | 502/230 |
| 5,017,541 | 5/1991 | Schmidt et al. | 502/230 |
| 5,358,919 | 10/1994 | Wu | 502/229 |

*Primary Examiner*—Glenn Caldarola
*Attorney, Agent, or Firm*—K. K. Brandes

[57] ABSTRACT

A catalyst composition is prepared by a method comprising impregnating alumina with at least one platinum compound, followed by treatment with at least one organoaluminum chloride (preferably ethylaluminum dichloride), titanium tetrachloride and at least one chloroalkane (preferably carbon tetrachloride). The thus-prepared catalyst composition is employed in the isomerization of saturated $C_4$–$C_8$ hydrocarbons (alkanes and/or cycloalkanes), preferably n-butane.

24 Claims, No Drawings

ISOMERIZATION CATALYST AND USE THEREOF IN ISOMERIZATION OF SATURATED HYDROCARBONS

BACKGROUND OF THE INVENTION

In one aspect, this invention relates to the preparation of a platinum-containing catalyst composition. In another aspect, this invention relates to the use of this novel catalyst composition as a catalyst for isomerizing saturated $C_4$–$C_8$ hydrocarbons.

Supported platinum/chlorine-containing catalyst compositions and their use in alkane isomerization reactions are well known, and are described in the patent literature, e.g., in U.S. Pat. Nos. 5,004,859 and 4,149,993. However, there are ever present incentives for the development of new, more effective Pt/Cl-containing catalyst compositions and new methods of preparing them.

SUMMARY OF THE INVENTION

It is an object of this invention to provide a novel method for preparing a supported, Pt/Cl-containing catalyst composition. It is another object of this invention to provide a novel catalyst composition prepared by this preparation method. It is a further object of this invention to employ this novel catalyst composition in reactions for isomerizing saturated $C_4$–$C_8$ hydrocarbon. Other objects and advantages will become apparent from the detailed description and the appended claims.

In accordance with this invention, a method of preparing a solid platinum- and chlorine-containing composition comprises:

(a) impregnating alumina with at least one platinum compound;

(b) heating the Pt-impregnated alumina obtained in step (a) at a temperature of about 300°–650° C. for a time period of at least about 5 minutes;

(c) heating the calcined material obtained in step (b) with a reducing gas at a temperature of about 200°–650° C. for a time period of at least 5 minutes;

(d) treating the calcined material obtained in step (c) with at least one organoaluminum chloride at a temperature of at least about 100° C. for a time period of at least about 5 minutes; and (e) treating the material obtained in step (d) with gaseous titanium tetrachloride and at least one gaseous chloroalkane at a temperature of about 250°–500° C. for a time period of at least about 10 minutes.

In one preferred embodiment, the at least one organoaluminum chloride is ethylaluminum dichloride. In another preferred embodiment, hydrogen gas is also present in chloriding step (e). In a further preferred embodiment, the chloroalkane is carbon tetrachloride. In still another preferred embodiment, the weight ratio of said at least one chloroalkane to $TiCl_4$ in step (f) is in the range of about 10:1 to about 500:1.

Also in accordance with this invention, a catalyst composition is provided which has been prepared by one of the preparation methods described above.

Further in accordance with this invention, at least one saturated feed hydrocarbon containing 4–8 carbon atoms per molecule selected from the group consisting of alkanes and cycloalkanes is isomerized to at least one corresponding saturated hydrocarbon isomer in the presence of hydrogen gas and a catalyst composition of this invention which has been prepared by the preparation method described above.

DETAILED DESCRIPTION OF THE INVENTION

(A) Catalyst Preparation

Any suitable alumina material can be used in step (a) of the preparation method of this invention. Suitable aluminas include (but are not limited to) hydrated aluminas (such as boehmite, pseudoboehmite, bayerite), alpha-alumina, beta-alumina, gamma-alumina, delta-alumina, eta-alumina and theta-alumina, preferably gamma-alumina. The alumina material generally has a surface area (determined by the BET method of Brunauer, Emmett and Teller employing $N_2$) of about 100–400 m²/g, a pore volume (measured by nitrogen instrusion porosimetry) of about 0.2–1.0 cm³/g, and a particle size of about 8–200 mesh. The alumina particles can be spherical, cylindrical, trilobal, or can have any other suitable shape. The presently preferred alumina particles are cylindrical extrudates.

Any suitable platinum compound which is water-soluble can be used in the preparation method of this invention. These compounds are well known and include (but are not limited to) platinum dichloride, platinum tetrachloride, hexachloroplatinic(IV) acid, ammonium hexachloroplatinate(IV), tetrammineplatinum(II) chloride, tetrammineplatinum(II) carbonate, tetrammineplatinum(II) hydroxide, dichlorodiammineplatinum(II), tetrachlordiammineplatinum(IV), platinum(II) nitrate, platinum(IV) nitrate, hexammineplatinum(II) nitrate, hexammineplatinum(IV) nitrate, diammineplatinum(IV) nitrite, diammineplatinum(II) oxalate, and many other complex or coordination compounds of divalent and tetravalent platinum. Presently preferred is hexachloroplatinic acid, $H_2PtCl_6$. The alumina material can be impregnated with at least one dissolved platinum compound in any suitable manner, e.g., by dissolving the Pt compound(s) in a polar solvent (preferably water) and then soaking or spraying the alumina with this solution. Generally about 0.1–1 (preferably about 0.2–0.4) weight-% Pt is incorporated into the alumina material.

Generally, the Pt-impregnated alumina material calcined in step (b) at a temperature of about 300°–650° C. (preferably 450°–600° C.) for a time period of about 0.5–20 hours (preferably about 2–4 hours). This calcining step can be done in an inert gas atmosphere (i.e., $N_2$, He, Ar) or in an $O_2$-containing atmosphere (e.g., air). Generally, the Pt-impregnated material is dried (preferably at about 80°–150° C.) before the calcination.

In step (c), the calcined Pt-impregnated alumina is heated in a reducing gas atmosphere (such as a gas which contains carbon monoxide and/or hydrogen), preferably hydrogen, at a temperature of about 200°–650° C. (more preferably about 300°–600° C.) for a time period of about 0.2–15 hours (more preferably about 0.5–5 hours).

In step (d) of the preparation method of this invention, the calcined Pt-containing alumina is contacted with at least one suitable organoaluminum chloride. Examples of such organoaluminum chlorides include (but are not limited to) methylaluminum dichloride, methylaluminum sesquichloride, dimethylaluminum chloride, ethylaluminum dichloride, ethylaluminum sesquichloride, diethylaluminum chloride, and mixtures thereof. Presently preferred is ethylaluminum dichloride. These organoaluminum compounds are easily hydrolyzed (by water) and thus should be handled and applied in a dry environment. Preferably, they are dissolved in a dry organic hydrocarbon solvent, such as in a $C_6$-$C_{10}$ cycloalkane, benzene, toluene, ethylbenzene, xylene(s) and the like. The presently preferred solvent is cyclohexane.

Generally, the weight ratio of the organoaluminum chloride to the Pt-impregnated alumina is in the range of about 0.05:1 to about 1:1, preferably about 0.1:1 to about 0.2:1. It is presently preferred to dissolve the organoaluminum chloride in an essentially water-free solvent, then contact the Pt-impregnated alumina with the solution (which generally contains about 5–50 weight-% of the organoaluminum chloride) at a temperature of about 10°–50° C. for a time period of about 0.5–5 hours (preferably about 0.5–2 hours), and finally heat the thus-treated Pt-impregnated alumina at a temperature of about 200°–800° C. (preferably about 500°–700° C.) for a time period of about 0.1–5 hours (preferably about 0.5–2 hours). However, it is within the scope of this invention to vaporize the organoaluminum chloride and contact the thus-vaporized compound with the Pt-impregnated alumina at the above-recited weight ratio for about 0.1–5 hours (preferably about 0.5–2 hours) at a temperature of about 200°–800° C. (preferably about 500°–700° C.). Step (d) is generally carried out in an inert gas atmosphere (e.g., $N_2$, He, Ar).

Chloriding step (e) is carried out by heating the treated material obtained in step (d) with vaporized $TiCl_4$ and with at least one vaporized chloroalkane. Preferably, hydrogen gas is also present in step (e). This treatment with $TiCl_4$ and chloroalkane(s) can be carried out sequentially in any order or essentially simultaneously, the latter being preferred. If the chloriding treatment with $TiCl_4$ and chloroalkane(s) is carried out sequentially, it is preferred to have hydrogen present in each chloriding substep. The treatment with $TiCl_4$ and chloroalkane(s) is generally carded out at a temperature of about 250°–500° C. (preferably about 300°–450° C.) for a period of time of about 0.2–20 hours (preferably about 0.5–2 hours). Generally, the weight ratio of chloroalkane(s) to $TiCl_4$ is in the range of about 10:1 to about 500:1, and preferably is in the range of about 50:1 to about 300:1. Preferably, the hydrogen pressure in step (e) is about 10–50 psig. Generally, hydrogen is used as the carder for transporting vaporized $TiCl_4$ and chloroalkane(s) to the solid material obtained in previous step (d). Generally, this material is present in a solid catalyst bed in a reactor tube where the chloriding occurs.

The chloroalkane employed in chloriding step (e) can be any suitable volatile chloroalkane. Generally, the chloroalkane contains 1–4 carbon atoms per molecule and 1–6 chlorine atoms per molecule. Examples of suitable chloroalkanes include (but are not limited to) chloromethane, dichloromethane, trichloromethane (chloroform), carbon tetrachloride, chloroethane, 1,1-dichloroethane, 1,2-dichloroethane, trichloroethanes, tetrachloroethanes, hexachloroethane, 1-chloropropane, 2-chloropropane, 1,2-dichloropropane, 1,3-dichloropropane, 2,2-dichloropropane, trichloropropanes, tetrachloropropanes, chlorobutanes, 1-chloro-2-methyl-propane, dichlorobutanes, trichlorobutanes, tetrachlorobutanes, and the like, and mixtures thereof. Carbon tetrachloride is presently preferred.

The finished catalyst composition generally contains about 0.05–0.5 (preferably about 0.1–0.3) weight-% Ti, about 0.1–1 (preferably about 0.2–0.4) weight % Pt and about 2–7 (preferably about 4–5) weight % Cl. The surface area, pore volume, shape and particle size of the finished catalyst composition are approximately the same as those of the alumina starting material (recited above).

(B) Isomerization Process

The catalyst of this invention is generally employed in the isomerization of saturated $C_4$-$C_8$ hydrocarbons (preferably normal alkanes). Examples of suitable feed hydrocarbons include (but are not limited to) normal butane, normal pentane, normal hexane, normal heptane, normal octane, cyclohexane, methylcyclopentane, cycloheptane, methylcycloheptane and the like, more preferably n-butane, generally in the presence of hydrogen. These so-called hydroisomerization processes are well known and have been described in the patent literature (e.g., in U.S. Pat. Nos. 4,149,993 and 5,004,859). Generally, hydrogen is mixed with the saturated hydrocarbon feed to form a feed mixture which is contacted with the isomerization catalyst of this invention contained in an isomerization zone. The concentration of the hydrogen in the feed mixture during this contacting step shall be such as to provide a hydrogen to saturated hydrocarbon molar ratio of at least about 0.01:1, generally about 0.01:1 to about 5:1, preferably about 0.02:1 to about 2:1. The basic isomerization reaction conditions are well known and can be varied to achieve the desired conversion of the feed hydrocarbon to the desired isomer in a manner known in the art. Also, the recovery of the product isomer from the reaction mixture can be carried out by any suitable separation technique, such as fractional distillation. Isomerization of normal butane (n-butane) to isobutane is the presently preferred reaction carried out with the catalyst composition of this invention.

Generally, the saturated feed hydrocarbon and $H_2$ are contacted with the catalyst (generally present in a fixed bed) at a reaction temperature of at least about 200° F., preferably at a temperature of about 200°–500° F. In the case of n-butane isomerization, the preferred reaction temperature is about 250°–400° F. Generally, the liquid hourly space velocity of the saturated hydrocarbon feed stream, i.e., cc of liquid feed hydrocarbon per cc of catalyst per hour, is about 0.1 to about 15. Generally, the reaction pressure is within the range of 200 psig to about 1500 psig in the isomerization zone. The gas hourly space velocity of the hydrogen feed stream is generally about 10–2,000 (preferably about 50–1,000) cc $H_2$ per cc catalyst per hour (so as to give the above-recited $H_2$:hydrocarbon ratio). In order to activate the catalyst and to retard its deactivation during the isomerization reaction, about 0.001 to about 1 weight percent chloride is frequently added to the alkane feed, generally in the form of at least one chloroalkane (described above), preferably carbon tetrachloride, chloroform, ethyl chloride or isopropyl chloride.

When the catalyst employed in the hydroisomerization process has lost its activity to the extent that the desired alkane conversion can no longer be attained at the desired reaction temperature, the catalyst can be reactivated by turning off the flow of the saturated feed hydrocarbon while maintaining the flow of the $H_2$ stream through the isomerization catalyst, generally at about the same gas hourly space velocity of $H_2$ and the same temperature conditions as in the isomerization reaction. In the preferred reactivation mode, hydrogen gas is passed through the partially deactivated isomerization catalyst bed at a temperature of about 50°–400° F. and a GHSV (gas hourly space velocity) of about 10–2,000 cc $H_2$ per cc catalyst per hour, for a time period of about 2 hours to about 10 days. Thereafter, the reactivated catalyst is redeployed in the isomerization process of this invention.

The following examples are presented to further illustrate the present invention and are not to be construed as unduly limiting the scope of this invention.

EXAMPLE I

This example illustrates the preparation of various alumina-supported platinum catalysts.

Catalyst A (Invention) was prepared by contacting 13.68 grams (20 cc) of a Pt/Al$_2$O$_3$ catalyst composition (containing about 0.3 weight-% Pt; surface area:215 m$^2$g; provided by UOP, Des Plaines, Ill.) with 17.0 grams of a 30 weight-% ethylaluminum dichloride (EADC) solution in cyclohexane in a stainless steel reactor tube under an helium gas atmosphere. The EADC solution was pumped into the reactor at a rate of about 1 cc/minute. The thus-treated material was heated in a helium gas stream at a temperature of about 650° C. for about 1 hour, and allowed to cool in a helium gas stream to 150° C. The flow rate of the helium stream was about 1 liter per minute.

Then 14.38 grams of the thus-obtained EADC-treated material were placed in stainless steel reactor and covered with a layer of Alundum® (inert alumina having a surface area of less than 1 m$^2$/g). The reactor and its contents were heated up to 300° C. (at a rate of 10° C. per minute) in a helium stream. Then the reactor and its contents were heated in a gas stream containing 70 volume-% He and 30 volume-% H$_2$ (flow rate of the gas stream: 1 liter/minute) for 10 minutes at 300° C. Thereafter, a mixture of 20 cc (32 g) CCl$_4$ and 0.131 g TiCl$_4$ was injected (at a rate of 1 cc of the mixture per minute) into the He/H$_2$ gas stream, and the entire reactor system was heated at 300° C. for 1 hour, followed by cooling in the He/H$_2$ gas stream to 150° C. Catalyst A had a Pt content of 0.30 weight-%.

Catalyst B (Invention) was prepared as follows. About 15 grams of alumina (provided by Criterion Catalyst Company, Houston, Tex.; sulfur content: 0%) was impregnated (by incipient wetness) with an aqueous solution of hexachloroplatinic acid (containing 0.26 gram of H$_2$PtCl$_6$, 16.4 grams of water and 0.34 grams of HCl). The thus-impregnated alumina was substantially dried by means of an aspirator pump for 3 hours, heated up in an oxygen gas stream to 525° C. at a rate of 2° C./minute, heated in the oxygen gas stream at 525° C. for 2 hours, cooled in a helium gas stream to 425° C., heated in a hydrogen gas stream at 425° C. for about 2 hours, and then cooled in hydrogen gas to 150° C.

15.0 grams (20 cc) of the reduced Pt/Al$_2$O$_3$ material was impregnated at room temperature with 7.0 grams of a 30 weight-% EADC solution (described for Catalyst A) under an argon atmosphere for about 16 hours. The thus-treated was heated up in a helium gas stream (flow rate: 1 liter/minute) to 650° C. within 1 hour, heated in the helium gas stream at 650° C. for 1 hour, and cooled in the He gas stream to 300° C. at a rate of 10° C./minute. Then a gas stream (flow rate 1 liter/minute) containing 70 volume-% He and 30 volume-% H$_2$ was passed through the reactor and its contents at 300° C. while a mixture of 20 cc (32 g) CCl$_4$ and 0.22 g TiCl$_4$ was injected into the He/H$_2$ gas stream (at a rate of 1 cc per minute). The entire reactor system was heated at 300° C. for about 1 hour, followed by cooling in the H$_2$/He gas stream to 150° C. Catalyst B had a Pt content of 0.32 weight-%.

Catalyst C (Invention) was prepared essentially in the same manner as Catalyst B, except that 0.22 g TiCl$_4$ was introduced with the He/H$_2$ gas stream about 10 minutes before the injection of 20 cc CCl$_4$ in the He/H$_2$ gas stream commenced. Catalyst C had a Pt content of 0.32 weight-%.

Catalyst D (Control) was prepared by impregnating 24.0 grams of air-calcined Pt/Al$_2$O$_3$ (Pt content: about 0.25 weight-%) with a 0.1 molar solution of TiCl$_4$ in n-pentane at room temperature, wherein the volume of the TiCl$_4$-containing impregnating solution was about equal to the volume of the Pt/Al$_2$O$_3$ material. The TiCl$_4$-impregnated material was separated from the impregnating solution, dried at room temperature by means of an aspirator pump, heated in an H$_2$/N$_2$ (volume ratio: about 1:1) gas mixture for 1 hour at 375° C., heated in CCl$_4$-saturated H$_2$ gas for 1 hour at 275° C., and heated in the H$_2$/N$_2$ mixture for 1 hour at 375° C. Catalyst D contained 0.23 weight-% Pt, 0.15 weight-% Ti and 2.6 weight-% Cl.

EXAMPLE II

This example illustrates the use of the catalyst materials described in Example I in the isomerization of n-butane.

20 cc of each catalyst was placed in a stainless steel reactor tube having an inner diameter of 1 inch and a length of 28 inches. The steel reactor tube was heated to 138° C. A stream of hydrogen gas was passed through the catalyst bed at a rate of 1.34 cubic feet per hour. The reactor pressure was about 500 psig, Liquid n-butane was introduced at a rate of 78.2 cc/hour (liquid hourly space velocity:3.9 cc/cc catalyst/hour), while the flow of the hydrogen gas stream was maintained at 1.34 ft$^3$/hour so as to provide a molar ratio of H$_2$ to n-butane of about 50:1. After the hydrogen/n-butane mixture had passed through the catalyst bed at the above conditions for about 10 minutes, carbon tetrachloride was injected into this feed mixture at a rate of 16 microliters per hour for a time period of up to about 24 hours. Thereafter, the CCl$_4$ feed rate was reduced to 6 microliters per hour, and the test was continued. The isomerization product was analyzed by means of a gas chromatograph. Pertinent catalyst preparation parameters and isomerization test results (obtained at comparable reaction times) are summarized in Table I.

TABLE I

| | Catalyst Preparation | | | Weight | n-Butane Isomerization | |
| --- | --- | --- | --- | --- | --- | --- |
| Catalyst | EADC Treatment | TiCl$_4$ Treatment | CCl$_4$ Treatment | Ratio of CCl$_4$ to TiCl$_4$ | Reaction Time (hr) | % of Isobutane in Product[2] |
| A (Invention) | Yes | Yes | Yes | 244:1 | 21 | 6.0 |
| B (Invention) | Yes | Yes | Yes | 145:1 | 22 | 10.6 |
| C (Invention) | Yes | Yes | Yes | 145:1 | 22 | 12.3 |
| D (Control) | No | Yes | Yes | 0 | 22 | 2.3 |
| I-8[1] | N/A[3] | N/A[3] | N/A[3] | N/A[3] | 20 | 12.9 |
| I-8[1] | N/A[3] | N/A[3] | N/A[3] | N/A[3] | 19 | 11.1 |

[1]Commercial Pt/Cl/Al$_2$O$_3$ catalyst for butane isomerization containing about 0.3 weight-% Pt and 3–4 weight-% Cl, marketed by UOP, De Plains, IL.

TABLE I-continued

|  | Catalyst Preparation | | | Weight | n-Butane Isomerization | |
|---|---|---|---|---|---|---|
|  |  |  |  |  | Reaction | % of |
| Catalyst | EADC Treatment | TiCl$_4$ Treatment | CCl$_4$ Treatment | Ratio of CCl$_4$ to TiCl$_4$ | Time (hr) | Isobutane in Product[2] |

[2]Based on isomerization product excluding H$_2$; isomerization conditions of all runs: amount of catalyst: about 20 cc (about 15 g); reaction temperature: about 138° C.; reaction pressure: about 500 psig; liquid n-butane feed rate: about 80 cc/hour; H$_2$ feed rate: about 1.3 ft$^3$/hr; H$_2$: n-butane mol ratio: about 10:1.
[3]No information on catalyst preparation available.

Test data in Table I show that invention catalysts A, B and C exhibited high n-butane isomerization activity (comparable to that of a commercial catalyst, UOP's I-8), whereas control Catalyst D (prepared without EADC treatment) was considerably less active.

Reasonable variations, modifications, and adaptations for various usages and conditions can be made within the scope of the disclosure and the appended claims without departing from the scope of this invention.

That which is claimed:

1. A method of preparing a solid platinum- and chlorine-containing composition comprising:

(a) impregnating alumina with at least one platinum compound;

(b) heating the Pt-impregnated alumina obtained in step (a) at a temperature of about 300°–650° C. for a time period of at least 5 minutes;

(c) heating the calcined material obtained in step (b) with a reducing gas at a temperature of about 200°–650° C. for a time period of at least about 5 minutes;

(d) treating the material obtained in step (c) with at least one organoaluminum chloride selected from the group consisting of methylaluminum dichloride, methylaluminum sesquichloride, dimethylaluminum chloride, ethylaluminum dichloride, ethylaluminum sesquichloride, diethylaluminum chloride and mixtures thereof at a temperature of at least about 100° C. for a time period of at least about 5 minutes; and (e) treating the material obtained in step (d) with gaseous titanium tetrachloride and at least one chloroalkane at a temperature of about 250°–500° C. for a time period of at least about 10 minutes.

2. A method in accordance with claim 1, wherein hydrogen gas is also present in treating step (e).

3. A method in accordance with claim 2, wherein about 0.1–1 weight-% Pt is incorporated into said alumina in step (a).

4. A method in accordance with claim 2, wherein step (b) is carried out for a time period of about 0.5–20 hours.

5. A method in accordance with claim 2, wherein step (c) is carried out for a time period of about 0.2–15 hours.

6. A method in accordance with claim 2, wherein step (d) is carried out at a weight ratio of said at least one organoaluminum chloride to the material obtained in step (c) of about 0.05:1 to about 1:1.

7. A method in accordance with claim 6, wherein said at least one organoaluminum chloride used in step (d) is ethylaluminum dichloride.

8. A method in accordance with claim 7, wherein step (d) is carried out at a temperature of about 200°–800° C. for a time period of about 0.1–5 hours.

9. A method in accordance with claim 7, wherein step (e) is carried out for a time period of about 0.2–20 hours at a weight ratio of said at least one chloroalkane to titanium tetrachloride of about 10:1 to about 500:1.

10. A method in accordance with claim 9, wherein said at least one chloroalkane used in step (e) is carbon tetrachloride.

11. A composition of matter prepared by the method of claim 1.

12. A composition of matter prepared by the method of claim 2.

13. A composition of matter prepared by the method of claim 7.

14. A composition of matter prepared by the method of claim 9.

15. A composition of matter prepared by the method of claim 10.

16. A composition of matter in accordance with claim 11, comprising about 0.05–0.5 weight-% Ti, about 0.1–1 weight-% Pt and about 2–7 weight-% Cl.

17. A method in accordance with claim 1, wherein said reducing gas used in step (c) is hydrogen.

18. A method in accordance with claim 17, wherein step (c) is carried out at a temperature of about 300°–600° C. for a time period of about 0.5–5 hours.

19. A method in accordance with claim 1, wherein said at least one chloroalkane employed in step (e) contains 1–4 carbon atoms and 1–6 chlorine atoms per molecule.

20. A method in accordance with claim 19, wherein said at least one chloroalkane is selected from the group consisting of chloromethane, dichloromethane, trichloromethane, carbon tetrachloride, chloroethane, 1,1-dichloroethane, 1,2-dichloroethane, trichloroethanes, tetrachloroethanes, hexachloroethane, 1-chloropropane, 2-chloropropane, 1,2-dichloropropane, 1,3-dichloropropane, 2,2-dichloropropane, trichloropropanes, tetrachloropropanes, chlorobutanes, 1-chloro-2-methylpropane, dichlorobutanes, trichlorobutanes, tetrachlorobutanes, and mixtures thereof.

21. A composition of matter prepared by the method of claim 6.

22. A composition of matter prepared by the method of claim 19.

23. A composition of matter in accordance with claim 16, comprising about 0.1–0.3 weight-% Ti.

24. A composition in accordance with claim 23, comprising 0.2–0.4 weight-% Pt.

* * * * *